United States Patent
Smith et al.

(10) Patent No.: US 9,468,368 B2
(45) Date of Patent: Oct. 18, 2016

(54) OPTICAL COUPLING EFFICIENCY DETECTION

(71) Applicant: Novartis AG, Basel (CH)

(72) Inventors: Ronald T. Smith, Irvine, CA (US); Ben Tse, San Diego, CA (US); Vit Ulinskas, Tustin, CA (US)

(73) Assignee: Novartis AG, Basel (CH)

( * ) Notice: Subject to any disclaimer, the term of this patent is extended or adjusted under 35 U.S.C. 154(b) by 56 days.

(21) Appl. No.: 14/468,696

(22) Filed: Aug. 26, 2014

(65) Prior Publication Data
US 2016/0058278 A1    Mar. 3, 2016

(51) Int. Cl.
| | |
|---|---|
| A61B 3/00 | (2006.01) |
| G02B 27/00 | (2006.01) |
| G01J 1/42 | (2006.01) |
| G01J 1/04 | (2006.01) |
| G01J 1/30 | (2006.01) |

(52) U.S. Cl.
CPC ............ A61B 3/0008 (2013.01); G02B 27/00 (2013.01); *G01J 1/0425* (2013.01); *G01J 1/30* (2013.01); *G01J 1/4257* (2013.01)

(58) Field of Classification Search
CPC ... A61B 3/0008; G02B 27/00; G01J 1/0425; G01J 1/30; G01J 1/4257
USPC ............... 351/221, 246; 385/115–121, 133; 356/73, 73.1, 123, 614, 615, 622, 624
See application file for complete search history.

(56) References Cited

U.S. PATENT DOCUMENTS

| | | | |
|---|---|---|---|
| 5,039,191 A * | 8/1991 | Myszka ............................ | 385/31 |
| 5,463,710 A * | 10/1995 | Filgas et al. .................... | 385/90 |
| 5,815,626 A | 9/1998 | Kuba et al. | |
| 7,292,323 B2 | 11/2007 | Artsyukhovich et al. | |
| 8,371,695 B2 | 2/2013 | Papac et al. | |
| 8,474,977 B2 | 7/2013 | Hahn et al. | |
| 8,542,962 B2 | 9/2013 | Smith et al. | |
| 8,561,280 B2 | 10/2013 | Diao et al. | |
| 8,662,670 B2 | 3/2014 | Papac et al. | |
| 9,107,730 B2 | 8/2015 | Huculak et al. | |
| 2001/0055462 A1* | 12/2001 | Seibel ............................ | 385/147 |
| 2008/0183160 A1 | 7/2008 | Papac et al. | |
| 2008/0269728 A1 | 10/2008 | Buczek et al. | |
| 2008/0291432 A1* | 11/2008 | Horvath et al. .............. | 356/73.1 |
| 2011/0292344 A1* | 12/2011 | Papac et al. ................... | 351/221 |
| 2012/0203075 A1* | 8/2012 | Horvath et al. .............. | 600/249 |
| 2015/0366432 A1 | 12/2015 | Artsyukhovich et al. | |

FOREIGN PATENT DOCUMENTS

| | | |
|---|---|---|
| EP | 1949877 B1 | 6/2012 |
| WO | 2016/032797 A1 | 3/2016 |

OTHER PUBLICATIONS

International Searching Authority, International Search Report, PCT/US2015/045641, Dec. 7, 2015, 5 pages.
International Searching Authority, Written Opinion of the International Searching Authority, PCT/US2015/045641, Dec. 7, 2015, 8 pages.
Bacher, Gerald David, Prosecution History, U.S. Appl. No. 14/571,389, filed Dec. 16, 2014, 67 pages.
Papac, Michael J., Prosecution History, U.S. Appl. No. 14/840,349, filed Aug. 31, 2015, 51 pages.

* cited by examiner

*Primary Examiner* — Jordan Schwartz
*Assistant Examiner* — George G King (57) ABSTRACT

An ophthalmic endo-illumination system includes a light source that produces a light beam, a fiber port that receives an optical fiber, a condenser that couples at least a portion of the light beam into the optical fiber received at the fiber port, and a beam splitter disposed between the fiber port and the condenser. The beam splitter is configured to receive the light beam from the condenser and split the light beam into a first beam which is coupled to the optical fiber and a second beam which is coupled to a monitoring fiber. An optical sensor is provided to detect an amount of the second beam output from the monitoring fiber. The coupling efficiency of the first beam coupled into the optical fiber may be determined based on the amount of the second beam output from the monitoring fiber.

19 Claims, 8 Drawing Sheets

OPTICAL COUPLING EFFICIENCY DETECTION

BACKGROUND

The devices, systems, and methods disclosed herein relate generally to the detection of coupling efficiency of a light beam directed into an optical fiber.

Ophthalmic endo-illumination probes are used to provide illumination in ophthalmic surgeries. In particular, an ophthalmic endo-illumination probe may be inserted into an eye to provide illumination inside the eye during an ophthalmic surgery. Typically, the ophthalmic endo-illumination probe is connected to an optical port of an ophthalmic endo-illumination system to receive light from the ophthalmic endo-illumination system. The ophthalmic endo-illumination system may include a light source that produces light and a condenser that couples the light into an optical fiber of the ophthalmic endo-illumination probe.

During the assembly of the optical port of the ophthalmic endo-illumination system, the position and tilt of the light beam from the condenser is adjusted until a coupling efficiency of the light beam into the ophthalmic endo-illumination probe connected at the optical port reaches an optimal value. Then, the assembly of the optical port is fixed or immobilized to maintain the coupling position and the coupling efficiency of the light beam into the ophthalmic endo-illumination probe. Nevertheless, various factors may cause the coupling position to move which results in a loss of coupling efficiency, such as shock and vibration imparted to the optical port assembly during shipment and setup, thermal-induced expansion, rotation and distortion of opto-mechanical mounts used to direct the light beam, thermal-induced motion of the optical fiber port, or beam motion caused by movement of adjustable reflective elements within the system, such as a rotatable or translatable variable beam splitters.

The present disclosure is directed to devices, systems, and methods that address one or more of the disadvantages of the prior art.

SUMMARY

In an exemplary aspect, the present disclosure is directed to an ophthalmic endo-illumination system. The ophthalmic endo-illumination system may include a light source that may produce a light beam, a fiber port that may receive an optical fiber, a condenser that may couple at least a portion of the light beam into the optical fiber received at the fiber port, and a beam splitter disposed between the fiber port and the condenser. The beam splitter may be configured to receive the light beam from the condenser and split the light beam into a first beam which is coupled to the optical fiber and a second beam which is coupled to a monitoring fiber. The ophthalmic endo-illumination system also may include an optical sensor configured to detect an amount of the second beam output from the monitoring fiber.

In an aspect, the ophthalmic endo-illumination system may include a processor configured to determine a coupling efficiency of the first beam at the optical fiber based on the amount of the second beam detected at the monitoring fiber. The processor also may be configured to, in response to detecting a decrease in the amount of the second beam at the monitoring fiber, control an actuator to move the condenser to re-align the coupling position of the first beam and the corresponding coupling position of the second beam.

In another exemplary aspect, the present disclosure is directed to an ophthalmic endo-illumination system including multiple fiber ports. The ophthalmic endo-illumination system may include a light source configured to produce a light beam, a source beam splitter configured to split the light beam into a first beam and a second beam, a first fiber port configured to receive a first optical fiber, a second fiber port configured to receive a second optical fiber, a first condenser configured to couple at least a portion of the first light beam into the first optical fiber received at the first fiber port, a second condenser configured to couple at least a portion of the second light beam into the second optical fiber received at the second fiber port, a first beam splitter disposed between the first fiber port and the first condenser. The first beam splitter may be configured to receive the first light beam from the first condenser and to split the first light beam into a third beam which is coupled into the first optical fiber and a fourth beam which is coupled into a first monitoring fiber.

The ophthalmic endo-illumination system also may include a second beam splitter disposed between the second fiber port and the second condenser. The second beam splitter may be configured to split the second light beam into a fifth beam which is coupled into the second optical fiber and a sixth beam which is coupled into a second monitoring fiber. The ophthalmic endo-illumination system further may include a first optical sensor configured to detect an amount of the fourth beam output from the first monitoring fiber and a second optical sensor configured to detect an amount of the sixth beam output from the second monitoring fiber.

A processor may be provided in the ophthalmic endo-illumination system to determine a first coupling efficiency of the third beam at the first optical fiber based on the amount of the fourth beam detected at the first monitoring fiber and a second coupling efficiency of the fifth beam at the second optical fiber based on the amount of the sixth beam detected at the first monitoring fiber. The ophthalmic endo-illumination system may further include a power monitor configured to detect an amount of the light beam produced at the light source.

The processor may be further configured to determine whether a decrease in the amount of the fourth beam detected at the first monitoring fiber is caused by a decrease in the first coupling efficiency at the first condenser or caused by a decrease in the amount of the light beam produced at the light source based on detection signals received from the power monitor, the first optical sensor, and the second optical sensor.

In still another exemplary aspect, the present disclosure is directed to a method including: coupling a light beam by a condenser through a beam splitter to split the light beam into a first beam which is coupled to an optical fiber of an ophthalmic endo-illumination probe and a second beam which is coupled to a monitoring fiber; detecting, by an optical sensor, an amount of the second beam output from the monitoring fiber; and determining a coupling efficiency of the first beam at the optical fiber based on the amount of the second beam detected at the monitoring fiber.

In an aspect, the method also may include generating a notification notifying a user when the coupling efficiency of the first beam at the optical fiber is below a predetermined value. Further, the method may include adjusting a position of the condenser to maintain the coupling efficiency of the first beam at a predetermined value.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The devices, systems, and methods described herein provide an ophthalmic endo-illumination system configured to detect an optical coupling efficiency of a light beam coupled into an ophthalmic fiber probe. In particular, the ophthalmic endo-illumination system may include a condenser that is configured to couple a light beam into a proximal end of the ophthalmic fiber probe connected to a fiber port of the ophthalmic endo-illumination system. A beam splitter is provided between the condenser and the fiber port to split the light beam into a first beam which is coupled into the ophthalmic fiber probe and a second beam which is coupled into a monitoring fiber. An optical sensor is provided to detect an amount of the second beam output from the monitoring fiber. Because the first beam and the second beam are parfocal except that the second beam is diverted by the beam splitter toward a different direction from the first beam, the coupling efficiency of the first beam into the ophthalmic fiber probe may be determined based on the amount of the second beam detected at the monitoring fiber.

In an embodiment, an actuator may be provided to adjust the position of the condenser to maintain the coupling efficiency of the first beam into the ophthalmic fiber probe. For example, when the ophthalmic endo-illumination system determines that the coupling efficiency is below a certain threshold, the ophthalmic endo-illumination system may control the actuator to adjust the position of the condenser to improve the coupling efficiency. As such, the ophthalmic endo-illumination system may provide an active feedback motion control system to continuously monitor and maintain the coupling efficiency.

Figure 1:
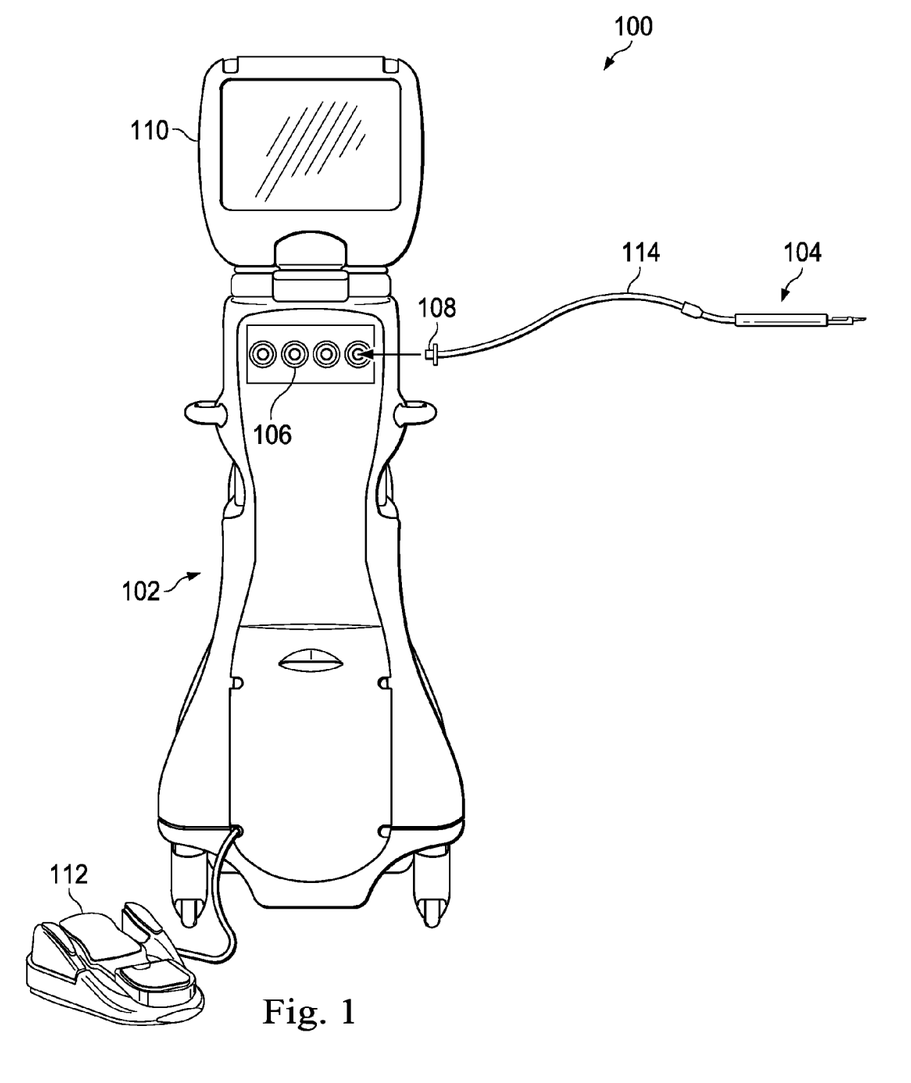
FIG. 1 illustrates a perspective view of an exemplary surgical system according to one embodiment consistent with the principles of the present disclosure.

FIG. 1 illustrates an exemplary surgical system, generally designated 100. The surgical system 100 may include a surgical utility supplying device 102 with an associated display screen 110 showing data relating to system operation and performance during a surgical procedure. The surgical system 100 also may include a surgical implement 104 configured to be connected to the surgical utility supplying device 102 via a surgical utility connector 108. The surgical utility supplying device 102 may supply various utility, such as imaging light, illumination light, compressed air, vacuum, pressurized liquid, or the like, to various kinds of surgical implements. For example, the surgical utility supplying device 102 may supply visible light to an ophthalmic fiber probe or may supply compressed air to a surgical vitrectomy probe. A user, e.g., a surgeon, may perform surgeries by using the surgical implements. The surgical utility supplying device 102 may include one or more utility ports 106 each configured to output a certain type of utility. For example, the surgical utility supplying device 102 may output a visible light to a fiber port configured to receive an ophthalmic fiber probe. Different types of utilities may be supplied from the surgical utility supplying device 102 to different types of surgical implements 104 at the same time.

The utility may be output from a utility port 106 to the surgical utility connector 108 and be carried by a tube fiber or cable (referenced herein as cable 114) to the surgical implement 104. The surgical implements 104 may selectively be attached or detached from the utility ports 106 by the surgical utility connectors 108. For example, a surgical implement 104 may be detached from the surgical utility supplying device 102 by detaching the surgical utility connector 108 from the utility port 106. The surgical utility supplying device 102 may detect a connection of a surgical implement 104 and may allow the supply of utility to the surgical implement 104 after the connection. The surgical system 100 also may include a foot pedal 112 connected to the surgical utility supplying device 102 for controlling the dispensing of utility from the surgical system 100. For example, a user may control the dispensing of the utility by selectively pressing and releasing the foot pedal 112.

Figure 2:
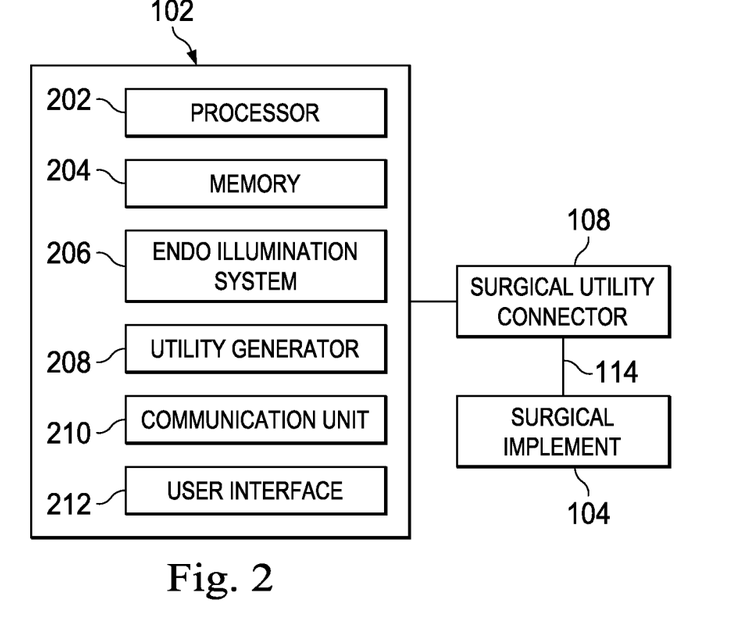
FIG. 2 illustrates a schematic diagram of a surgical system according to an aspect consistent with the principles of the present disclosure.

FIG. 2 illustrates a schematic diagram of an exemplary surgical utility supplying device, e.g., the surgical utility supplying device 102. The surgical utility supplying device 102 may include a processor 202 configured to perform calculation and determination for controlling various operations of the surgical utility supplying device 102. The processor 202 may receive various signal inputs and make various determinations based on the signal inputs. For example, the processor 202 may receive signals from an optical sensor configured to detect an amount of a light output to determine a coupling efficiency of a light beam into an optical fiber. The processor 202 also may control the display screen 110 to display various information regarding the operations of the surgical utility supplying device 102 to notify various information to the user.

The surgical utility supplying device 102 may include a memory 204 configured to store information permanently or temporarily for various operations of the surgical utility supplying device 102. For example, the memory 204 may store programs that may be executed by the processor 202 to perform various functions of the surgical utility supplying device 102. The memory 204 also may store various data relating to operation history, user profile or preferences, various operation and surgical settings, and the like. Programs and information stored in the memory 204 may continuously be updated to provide customization and improvement in the operation of the surgical utility supplying device 102. The memory 204 also may include programs and information relating to operational parameters for coupling efficiency at different fiber ports.

The surgical utility supplying device 102 also may include an endo-illumination system 206. The endo-illumination system 206 may include optical components configured to couple a light beam into an ophthalmic fiber probe connected at a utility port, e.g., fiber port, of the surgical utility supplying device 102. In particular, the endo-illumination system 206 may include a collimator configured to receive light from a light source and collimate the light into a light beam, spectral filters configured to filter the light beam into desired spectrums, and a condenser configured to couple the light beam into an optical fiber of the ophthalmic fiber probe.

The surgical utility supplying device 102 may include a utility generator 208. The utility generator 208 may include motors, light emitting devices, pumps, and the like that may generate various utilities, such as illuminating light, imaging light, pressured liquid, compressed air, and the like. In an embodiment, the utility generator 208 may be connected to an external utility source to receive utility externally. For example, the utility generator 208 may be connected to a vacuum source or an air compressor to receive vacuum or compressed air. The utility generator 208 may supply various utilities to respective utility ports 106.

The surgical utility supplying device 102 may include a communication unit 210. The communication unit 210 may include various communication devices, such as Ethernet card, wi-fi communication device, telephone device, digital I/O (Input-Output) ports or the like, that may allow the surgical utility supplying device to send and receive information to and from other devices. For example, the communication unit 210 may receive input from other surgical devices to coordinate a surgical operation. In another example, the communication unit 210 may transmit and receive messages or notifications, such as email, text, or other messages or notifications to a user's mobile device to notify certain information to the user.

The surgical utility supplying device 102 also may include a user interface 212. The user interface 212 may include user input devices, such as a keyboard, a touch screen, the foot pedal 112, a mouse, a microphone, or the like that allow a user to input instructions to the surgical utility supplying device 212. For example, the user may enter parameters for a utility and operate the foot pedal 112 to dispense the utility to the surgical implement 104. The user interface 212 also may include user output devices, such as a display screen 110, an audio speaker, LED (light-emitting diode) lights, or other visual or tactile signals that convey information to a user. For example, an audio speaker may emit an alarm when a coupling efficiency at a particular fiber port drops below a certain threshold during a surgical operation. Thus, the user interface 212 enables a user to interact with the surgical utility supplying device 102 during surgical operations.

Figure 3:
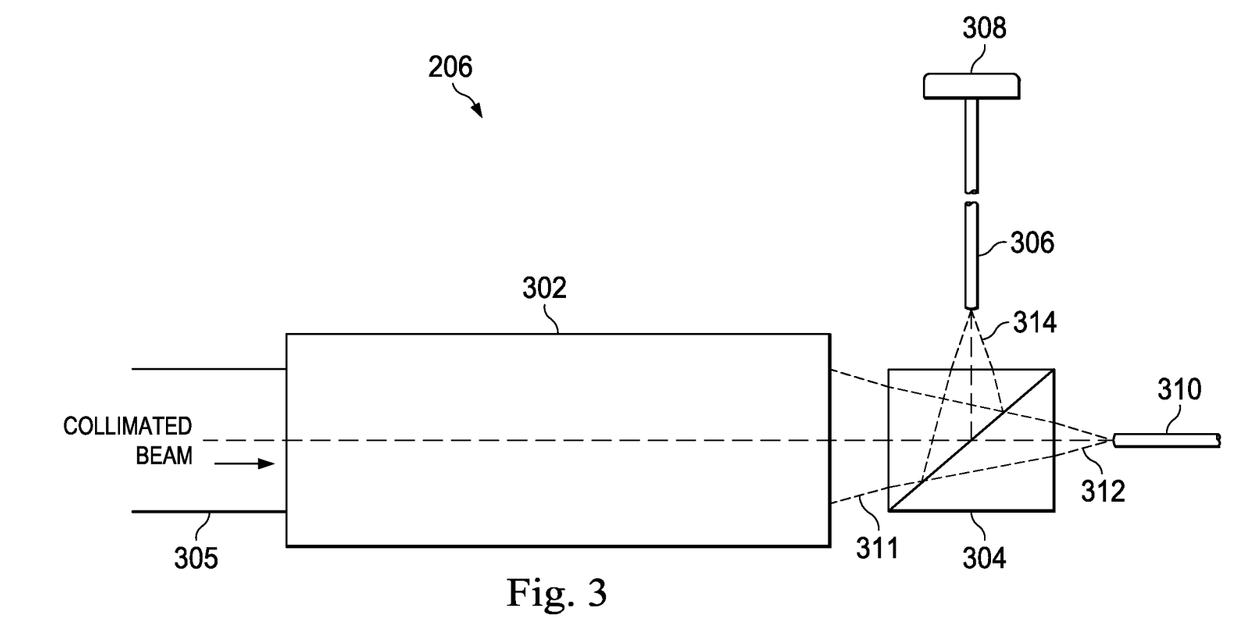
FIG. 3 illustrates a schematic diagram of an exemplary ophthalmic endo-illumination system according to an aspect consistent with the principles of the present disclosure.

FIG. 3 illustrates a schematic diagram of an ophthalmic endo-illumination system 206 according to one embodiment. The ophthalmic endo-illumination system 206 may include a condenser 302 configured to receive a light beam 305. In particular, a light source (not shown in FIG. 3) may produce a light which may be collimated into a light beam 305 by a collimator (not shown). The condenser 302 may receive the light beam 305 and couple the light beam 305 into an optical fiber 310 of a surgical implement 104, e.g., an ophthalmic fiber probe, connected to the utility port 106, e.g., a fiber port.

The ophthalmic endo-illumination system 206 may include a beam splitter 304 disposed between the condenser 302 and the optical fiber 310 and configured to split a light beam 311 from the condenser 302 into a first beam 312 and a second beam 314. For example, the beam splitter 304 may receive the coupled light beam from the condenser 302 and transmit a portion of the light beam while reflecting a portion of the light beam. As such, the first beam 312 is transmitted to continue to reach the optical fiber 310. Thus, the first beam 312 may be coupled into the optical fiber 310. The second beam is reflected or diverted in a different direction, e.g., a perpendicular direction from the first beam, toward a monitoring fiber 306. Thus, the second beam may be coupled into the monitoring fiber 306.

The beam splitter 304 may be a beam splitter cube or any other optical device configured to receive a light beam and split the light beam into two different light beams. The beam splitter 304 may receive the light beam and divert a portion of the light beam, e.g., between 0.8% to 1.5% of the beam power, into the second beam 314. The main portion of the light beam, e.g., between 99.2% to 97.5% of the beam power, may be transmitted straight into the optical fiber 310 of the ophthalmic fiber probe. In an exemplary embodiment, the optical fiber 310 is a 25 µm core and 0.26 NA multimode optical fiber with a 7 µm tolerance core diameter. In other embodiments, optical fibers with different diameters or sizes may be used.

The second beam 314 may be focused into the monitoring fiber 306. The monitoring fiber 306 may have a smaller core diameter than that of the optical fiber 310. For example, one exemplary embodiment of a monitoring fiber 306 is a 4.3 µm core and 0.12 NA single-mode optical fiber. The monitoring fiber 306 may receive the second light beam 314 at a proximal end. The second light beam 314 may propagate within the monitoring fiber 306 and exit at a distal end of the monitoring fiber 306. The monitoring fiber 306 may have a length of several inches such that any light modes from the cladding of the monitoring fiber 306 are substantially eliminated. An optical sensor 308 may be provided at the distal end of the monitoring fiber 306 to detect the power or amount of the second beam 314 at the distal end.

The beam splitter 304, the proximal end of the monitoring fiber 306, and the proximal end of the optical fiber 310 may be arranged in a particular manner such that the first beam and the second beam are parfocal except that the second beam 314 is folded. For example, if the folded second beam 314 were unfolded, the second beam 314 and the first beam 312 may coincide in space. In particular, if unfolded, the second beam 314 and the position of the entrance aperture of the monitoring fiber 306 may coincide in space with the first beam 312 and the entrance aperture of the optical fiber 310. Thus, a coupling position and/or coupling efficiency of the first beam 312 at the proximal end of the optical fiber 310 may directly correspond to the coupling position and/or coupling efficiency of the second beam 314 at the proximal end of the monitoring fiber 306. Therefore, by monitoring the amount of the second beam 314 at the monitoring fiber 306, the coupling efficiency of the first beam 312 at the optical fiber 310 may be determined.

Figure 4:
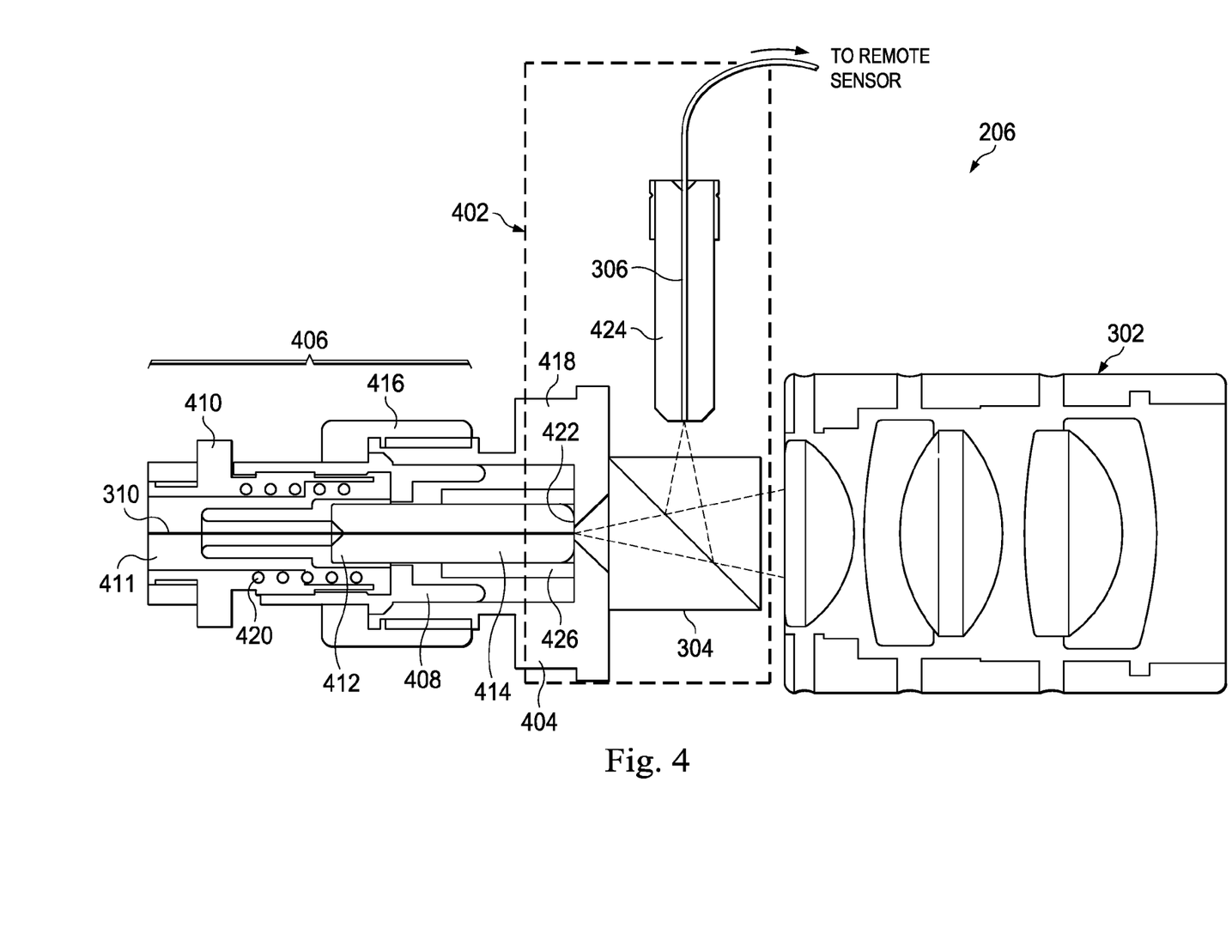
FIG. 4 illustrates a detailed schematic diagram of an exemplary ophthalmic endo-illumination system according to an aspect consistent with the principles of the present disclosure.

FIG. 4 illustrates a detailed schematic diagram of an exemplary ophthalmic endo-illumination system according to an embodiment. As shown in FIG. 4, the ophthalmic endo-illumination system 206 may include the condenser 302 which may include one or more optical lenses or other optical components configured to focus a light beam. The ophthalmic endo-illumination system 206 may include a fiber port 404, which may be one of the utility ports 106, as shown in FIG. 1. The fiber port 404 may be configured to receive a fiber connector 406, e.g., the utility connector 108 as shown in FIG. 1. The fiber connector 406 may connect the optical fiber 310 to the fiber port 404. The optical fiber 310 may extend within the cable 114 (FIG. 1) and may guide a light beam to the surgical implement 104 (FIG. 1), such as an endo-illuminator probe. The fiber connector 406 may be removable from the fiber port 404 to disconnect the endo-illuminator probe from the ophthalmic endo-illumination system 206.

The fiber connector 406 may include a front body 408 and a rear body 410. A channel 411 may be formed through each of the front body 408 and the rear body 410. A ferrule 414 may be provided within the channel 411. The optical fiber 310 may be accommodated in the ferrule 414. The fiber port 404 may include a cylindrical recess configured to receive the front body 408 of the fiber connector 406. The cylindrical recess may be formed by a cylindrical wall 418 which may surround a portion of the front body 408 of the fiber connector 406 when the fiber connector 406 is connected to the fiber port 404.

The fiber connector 406 may include a nut 416 including female thread on its inner surface which may interact with male threads provided on an outer surface of the cylindrical wall 418 of the fiber port 404 to secure the fiber connector 406 at the fiber port 404. The cylindrical recess of the fiber port 404 may include an inner end surface 422. An opening may be formed through the inner end surface 422 through which a light beam may project to be coupled into the optical fiber 310. When the fiber connector 406 is connected to the fiber port 404, a proximal end surface of the ferrule 412 may abut against the inner end surface 422 such that a proximal end surface of the optical fiber 310 is positioned at the opening of the inner end surface 422. A sleeve 426 may be provided to accommodate and to position the ferrule 412, such that the proximal end of the optical fiber 310 is precisely positioned at the opening of the inner end surface 422. The sleeve 426 may be formed with a material that is not easily deformed or change shape, such that the ferrule 412 and the optical fiber 310 may be positioned precisely at the opening of the inner end surface 422. A spring 420 may be provided in the fiber connector 406 to exert a biasing force on the ferrule 412 to tightly abut the ferrule 412 against the inner end surface 422 of the fiber port 404.

The beam splitter 304 may be provided between the condenser 302 and the fiber port 404. The beam splitter 304 may abut against the fiber port 404. In an embodiment, a space may be provided between the beam splitter 304 and the fiber port 404. The monitoring fiber 306 may be provided in a ferrule 424. The ferrule 424 may be positioned above the beam splitter 304. As noted above, the ferrule 424, the fiber port 404, and the beam splitter 304 may be positioned in a manner that results in a parfocal relationship between a transmitted light beam and a reflected light beam from the beam splitter 304. As such, a deviation from a coupling position at the fiber port 404 corresponds to a deviation from a coupling position at the monitoring fiber 306.

The monitoring fiber 306 in the ferrule 424, the fiber port 404, and the beam splitter 304 may be provided in an athermalized assembly 402, shown as a dashed line area in FIG. 4, within which the optical characteristics of the assembly, such as the parfocal relationship, remain the same in changing temperatures. For example, the athermalized assembly may maintain the same optical characteristics between 10° C. and 35° C.

Figure 5:
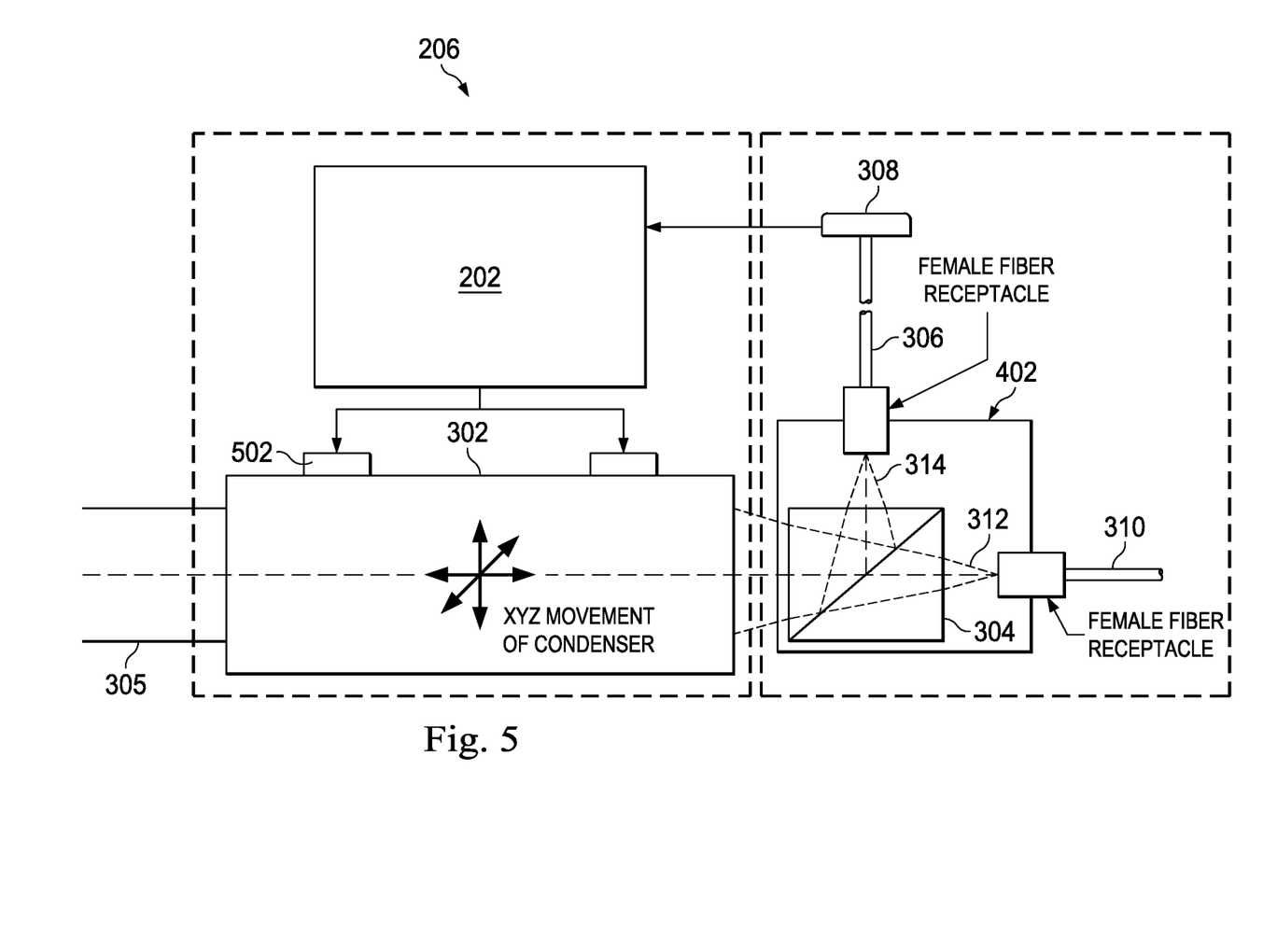
FIG. 5 illustrates a schematic diagram of an exemplary ophthalmic endo-illumination system including an actuator according to an aspect consistent with the principles of the present disclosure.

FIG. 5 illustrates a schematic diagram of an exemplary ophthalmic endo-illumination system including an actuator according to an embodiment. The ophthalmic endo-illumination system 206 in FIG. 5 is substantially the same as that of FIG. 3 with the addition of an actuator 502. In particular, the actuator 502 may be disposed at the condenser 302 to change a position or orientation of the condenser 302. The actuator 502 may be a piezo-electric actuator, a MEMS (microelectromechanical systems) actuator, or any actuator configured to provide precise movement to the condenser 302.

In one exemplary arrangement, the actuator 502 includes three sets of actuating mechanisms configured to move the condenser 302 in the X, Y, and Z axis or directions. The X direction may be a lateral horizontal direction perpendicular to the Z direction, the Y direction may be a direction perpendicular to the X direction or a lateral vertical direction, and the Z direction may be an axial horizontal direction toward or away from the beam splitter 304. In an embodiment, the condenser 302 may be disposed on a xyz-translation stage and the actuator 502 may move the translation stage to move the condenser 302.

The actuator 502 may be controlled by the processor 202 to move the condenser 302 to improve the coupling efficiency. In particular, the processor 202 may receive a signal from the optical sensor 308 indicating the amount of the second beam 314 detected at the monitoring fiber 306. If the amount of the second beam 314 drops below a certain threshold, the processor 202 may determine that there is a loss of coupling sufficiency at the monitoring fiber 306 and similarly at the optical fiber 310. Thus, the processor 202 may generate and send control signals to the actuator 502 to adjust the coupling position by moving the condenser 302. The actuator 502 may move the condenser 302 various manners, such as in both directions in each of the X, Y, and Z axis, tilting in various orientations, rotating, and the like. The processor 202 may continue to analyze the signals received at the optical sensor 308 at various positions or orientations of the condenser to find the position or orientation that result in optimal coupling efficiency at the monitoring fiber 306 which also correspond to the optimal coupling efficiency at the optical fiber 310.

Figure 6:
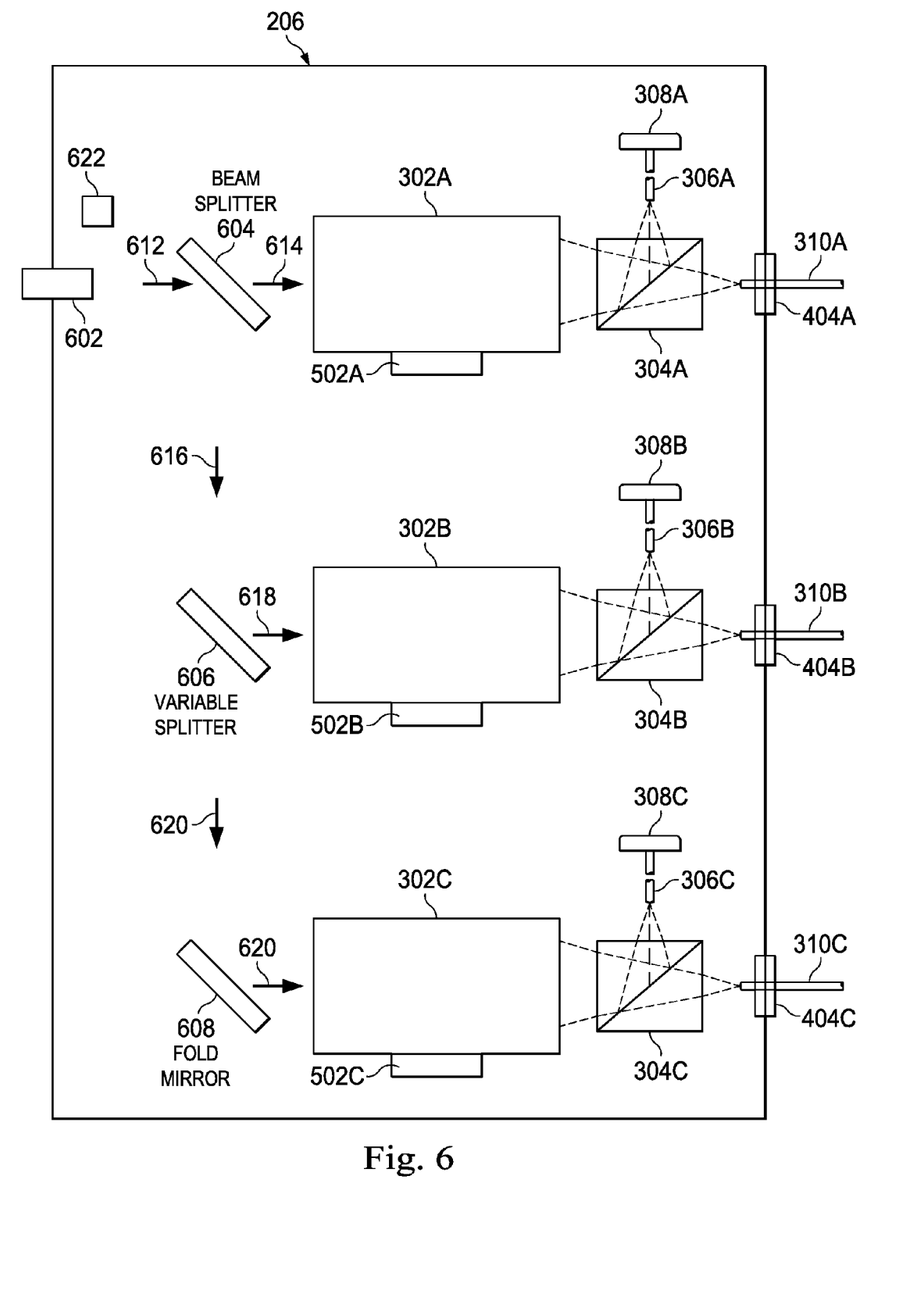
FIG. 6 illustrates a schematic diagram of an exemplary ophthalmic endo-illumination system including multiple fiber ports according to an aspect consistent with the principles of the present disclosure.

FIG. 6 illustrates a schematic diagram of an exemplary ophthalmic endo-illumination system including multiple fiber ports according to an embodiment. The ophthalmic endo-illumination system 206 may include multiple fiber ports 404. For example, as shown in FIG. 6, three fiber ports 404A, 404B, and 404C may be provided to supply illumination light to three different optical fibers 310A, 310B, and 310C, respectively. In particular, three sets of condensers 302A, 302B, 302C, beam splitters 304A, 304B, 304C, monitoring fibers 306A, 306B, and 306C, optical sensors 308A, 308B, and 308C, and actuators 502A, 502B, and 502C may be provided respectively at the fiber ports 404A, 404B, and 404C. Thus, coupling efficiency may be detected at each of the three fiber ports 404A, 404B, and 404C and the coupling efficiency at respective fiber ports 404A, 404B, and 404C may actively be independently adjusted to maintain their respective coupling efficiency. Although FIG. 6 illustrates three fiber ports, it is understood that any number of fiber ports may be implemented. For example, an n number of ports may be implemented, where n is any integer.

In an embodiment, a light source 602 may produce a light 612 to be used at the three fiber ports 404A, 404B, and 404C. The light 612 produced at the light source 602 may first be split into two light beams 614 and 616 by a beam splitter 604. The light beam 614 may be directed to the condenser 302A to be coupled to the optical fiber 310A at the fiber port 404A. The fiber port 404A may output high power illumination light, because the light beam 614 may include a main portion of the light 612 produced at the light source 602.

Light beam 616 may be split into light beams 618 and 620 by a variable splitter 606. Light beam 618 may be directed to the condenser 302B to be coupled to the optical fiber 310B at the fiber port 404B. Further, light beam 620 may be directed to a fold mirror 608 which may direct the light beam 620 to the condenser 302C to be coupled to the optical fiber 310C at the fiber port 404C. Thus, the light source 602 may supply light to three different fiber ports 404A, 404B, and 404C. A power monitor 622 may be disposed at the light source 602 to detect the light output from the light source 602.

Detection signals from the power monitor 622 and the optical sensors 306A, 306B, and 306C may be received by the processor 202 of the surgical system utility supplying device 102. The processor 202 may analyze the signals to determine the cause of a loss of illumination light at each fiber ports 404A, 404B, and 404C. For example, if optical sensor 308A detects a drop of light output at monitoring fiber 306A and the power monitor 622 detects no change in the light output from the light source 602, then the processor 202 may determine that the reduction in the light output at the monitoring fiber 306A may be caused by a loss of coupling efficiency at the fiber port 404A. Thus, the processor 202 may control the actuator 502A to adjust the position or orientation of the condenser 302A to improve the coupling efficiency at the fiber port 404A.

On the other hand, if optical sensors 308A, 308B, and 308C all detect a drop in light output at respective monitoring fibers 306A, 306B, and 306C and the power monitor 622 also detect a drop in the light output at the light source 602, then the processor may determine that the reduction in the light output at the monitoring fibers 306A, 306B, and 306C may be caused by a loss of light output at the light source 602. As such, no adjustment at the condensers 302A, 302B, and 302C is performed.

Figure 8:
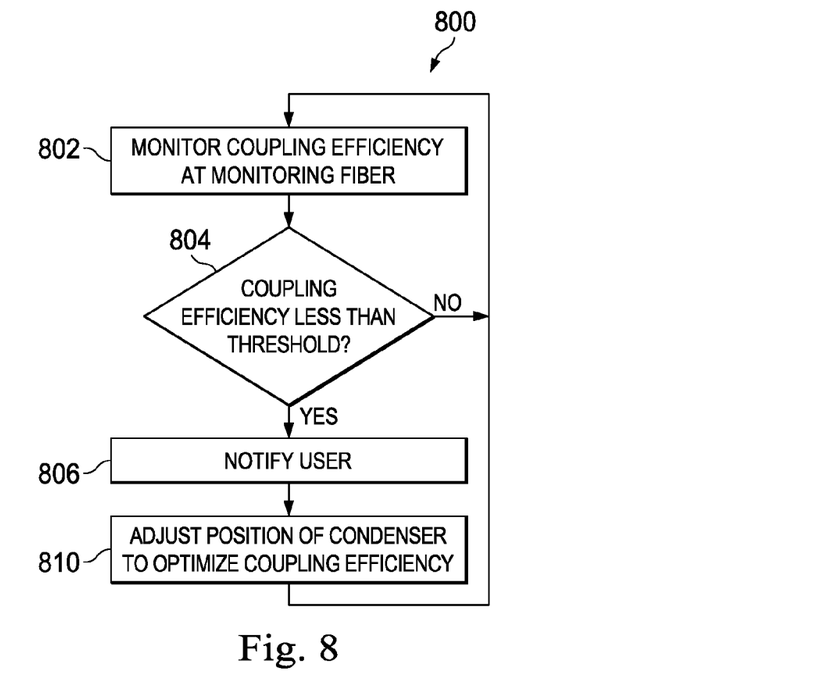
FIG. 8 is a flow chart illustrating a method for detecting a coupling efficiency of an optical fiber according to an aspect consistent with the principles of the present disclosure.

FIG. 8 is a flow chart illustrating a method for detecting a coupling efficiency of an optical fiber according to an embodiment. At 802, the ophthalmic endo-illumination system 206 may monitor coupling efficiency at one or more fiber ports 404. In particular, optical sensor 308 may continuously detect the light output from monitoring fiber 306. The detection signal from the optical sensor 308 may be forwarded to the processor 202 to be analyzed.

At 804, the processor 202 may determine whether there is a drop in coupling efficiency by determining whether the signal output from the optical sensor 308 drops below a certain threshold. If not, the process 800 may return back to 802 to continue monitoring the output of the monitoring fiber 305. If so, the processor 202 may determine the cause of the drop in output amount at the monitoring fiber 306. If the output from the light source 602 detected at the power monitor 622 remains substantially the same, then the drop in output amount at the monitoring fiber 306 likely is caused by a loss in coupling efficiency at the fiber port 404. On the other hand, if the output from the light source 602 detected at the power monitor 622 has a drop in power, the processor 202 may determine that the loss of output amount at the monitoring fiber 306 is caused by a drop in the output of the light source 602.

At 806, the processor 202 may notify the user of the detected output and/or the change in the detected output. For example, the processor 202 may generate a message notifying the user that there is a loss of light output at a certain fiber port 404 and the reason for the loss of light output, such as faulty light source, misalignment of coupling position at the fiber port 404, or the like. In some examples, the processor stores a threshold coupling efficiency value and if the threshold value is passed, then the processor notifies the user. The threshold may be an upper threshold or a lower threshold. The notification may be one or more of a message displayed on the display screen 110, an audible voice stating the message, an audible warning sound emitted from the surgical system 100, a visual warning, such as a flashing light, and the like. Thus, the user may be notified to address the problem. For example, the user may switch out the light source, recalibrate the coupling position, or take other actions. In an embodiment, the notification may notify the user that the surgical system 100 is automatically re-aligning the coupling position to address the problem. Thus, the user may be notified to wait for the surgical system 100 to finish the re-alignment process.

At 810, if there is a loss in coupling efficiency at the fiber port 404, the processor may control the actuator 502 to move the condenser 302 to adjust the coupling position at the fiber port 404. In particular, the processor 202 may first determine a range or an area at the fiber port 404 to scan for the optimal coupling position. The processor 202 may then control the actuator 502 to move incrementally in X, Y, and Z directions to find the optimal coupling position. For example, the processor 202 may move the condenser 302 incrementally in each of the X, Y, and Z direction to scan a plurality of different positions within the range or area. The light output detected at the monitoring fiber 306 at each of these positions may be recorded and compared to find the position with the highest output. The optimal coupling position may be a position at which the light output at the monitoring fiber 306 would decrease when the condenser 302 is moved away from that position in either X, Y, or Z directions.

Figure 7:
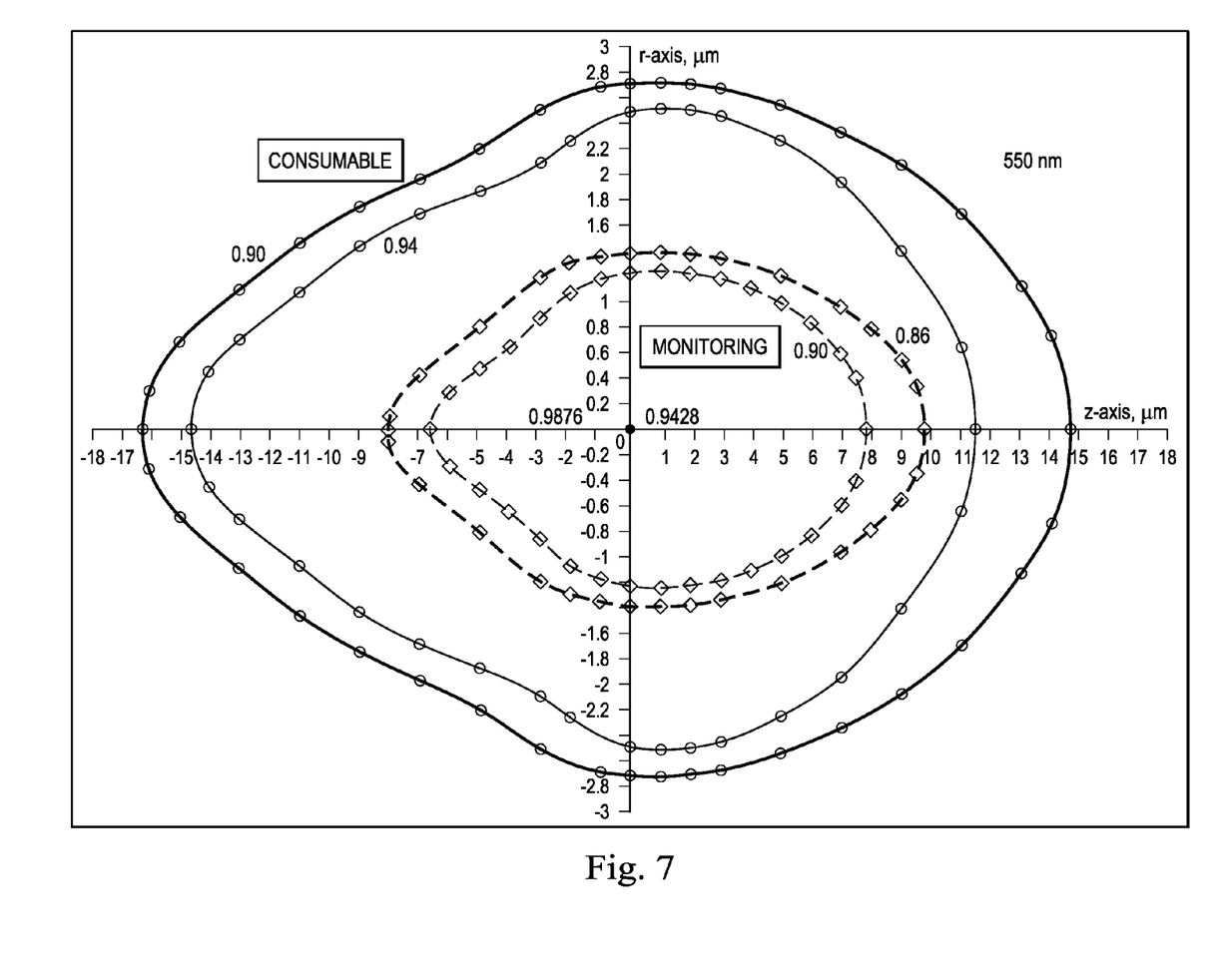
FIG. 7 illustrates a coupling efficiency map for an optical fiber and a monitoring fiber according to an aspect consistent with the principles of the present disclosure.

In an embodiment, the monitoring fiber 306 may have a smaller core diameter than that of the optical fiber 310 of the ophthalmic fiber probe. As such, the monitoring fiber 306 is more sensitive to the loss of coupling efficiency than the optical fiber 310, because the monitoring fiber 306 has a smaller entrance surface at which the light beam may enter. This may enable the system to detect any misalignment or deviation to the monitoring fiber 306 before it is noticeable at the optical fiber 310. Thus, the system may correct this misalignment or deviation before the coupling efficiency deteriorates at the optical fiber 310. FIG. 7 is an exemplary contour map of the relative fiber coupling efficiency vs. axial (z) misalignment and lateral (r) misalignment for the optical fiber 310 and the monitoring fiber 306. As shown in FIG. 7, the relative coupling efficiency falls off more rapidly with axial and/or lateral misalignment for the monitoring fiber 306 than it does for the optical fiber 310, e.g., consumable fiber. This feature may enable the system to detect at the monitoring fiber 306 that a misalignment is starting to occur and correct the misalignment before the coupling efficiency at the optical fiber 310 is affected.

Figure 9:
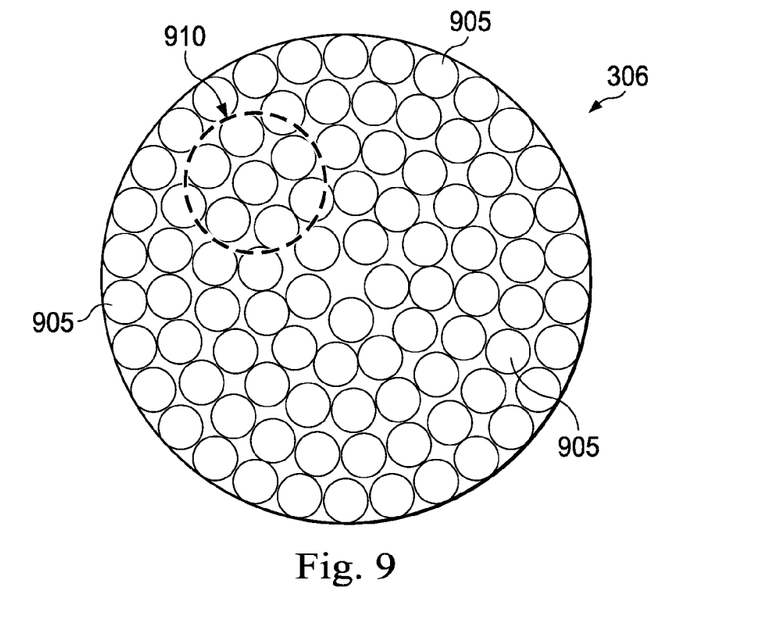
FIG. 9 illustrates a perspective view of a monitoring fiber including an array of optical fibers according to an aspect consistent with the principles of the present disclosure.

In an embodiment, the monitoring fiber 306 may include a two-dimensional array of single-mode fibers. For example, as shown in FIG. 9, the monitoring fiber 306 may include a plurality of optical fibers 905 with core diameter smaller than that of the optical fiber 310. The optical sensor 308 may detect light output from each of the array of the fibers. By evaluating the change in light output for each of the fibers, the processor 202 may determine in which direction (x, y, or z) the coupling position of the beam spot 910, is misaligned. As shown in FIG. 9, the beam spot 910, shown in dashed line, is deviating toward the left side of FIG. 9. Thus, the optical sensor 308 may detect higher output from optical fibers 905 around the left side. The processor 202 may control the actuator 502 to move the beam spot 910 back toward the center region of the monitoring fiber 306. As such, the two-dimensional array of optical fibers may provide additional information regarding the direction of misalignment to allow proper correction.

Accordingly, the above embodiments provide a system or method for implementing detection of coupling efficiency in an ophthalmic endo-illumination system. In particular, a beam splitter is provided to divert a portion of the coupling light beam to a monitoring fiber. The coupling efficiency may be determined based on the light output detected at the monitoring fiber. Further, a processor may control an actuator to move a condenser to improve the coupling efficiency.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. An ophthalmic endo-illumination system comprising:
a light source configured to produce a light beam;
a fiber port configured to interface with an optical fiber;
a condenser configured to couple at least a portion of the light beam into the optical fiber at the fiber port;
a beam splitter disposed between the fiber port and the condenser, wherein the beam splitter is configured to receive the light beam from the condenser and split the light beam into a first beam which is coupled to the optical fiber and a second beam which is coupled to a monitoring fiber; and
an optical sensor configured to detect an amount of a second beam output from the monitoring fiber;
wherein the monitoring fiber comprises a plurality of fibers, and
wherein the optical sensor is configured to detect a position of the second beam among the plurality of fibers.

2. The ophthalmic endo-illumination system of claim 1, wherein the beam splitter is configured to divert the second beam in a direction perpendicular to the first beam.

3. The ophthalmic endo-illumination system of claim 1, wherein the monitoring fiber has a smaller diameter than that of the optical fiber.

4. The ophthalmic endo-illumination system of claim 1, wherein a distance between the beam splitter and a beam receiving end of the optical fiber is the same as a distance between the beam splitter and a beam receiving end of the monitoring fiber.

5. The ophthalmic endo-illumination system of claim 1, wherein the beam splitter is configured to split the light beam into the first and the second beams with a predetermined ratio.

6. The ophthalmic endo-illumination system of claim 1, wherein the beam splitter, the fiber port, and the monitoring fiber are disposed in an athermalized assembly.

7. The ophthalmic endo-illumination system of claim 1 further comprising an endo-illuminator fiber probe within which the optical fiber is disposed, wherein the endo-illuminator fiber probe is connected to the fiber port to receive the first beam.

8. The ophthalmic endo-illumination system of claim 1 further comprising a processor configured to determine a coupling efficiency of the first beam at the optical fiber based on the amount of the second beam output detected at the monitoring fiber.

9. The ophthalmic endo-illumination system of claim 8 further comprising an actuator configured to move the condenser to adjust a coupling position of the first beam and to correspondingly adjust a coupling position of the second beam.

10. The ophthalmic endo-illumination system of claim 9 wherein the processor is configured to, in response to detecting a decrease in the amount of the second beam output at the monitoring fiber, control the actuator to move the condenser to re-align the coupling position of the first beam and the corresponding coupling position of the second beam.

11. The ophthalmic endo-illumination system of claim 10, wherein the coupling position is re-aligned when the amount of the second beam output detected at the monitoring fiber returns back to a predetermined value.

12. The ophthalmic endo-illumination system of claim 1, wherein the beam splitter comprise a beam splitter cube.

13. An ophthalmic endo-illumination system comprising:
a light source configured to produce a light beam;
a source beam splitter configured to split the light beam into a first beam and a second beam;
a first fiber port configured to interface with a first optical fiber;
a second fiber port configured to interface with a second optical fiber;
a first condenser configured to couple at least a portion of the first light beam into the first optical fiber at the first fiber port;

a second condenser configured to couple at least a portion of the second light beam into the second optical fiber at the second fiber port;
a first beam splitter disposed between the first fiber port and the first condenser, wherein the first beam splitter is configured to receive the first light beam from the first condenser and to split the first light beam into a third beam which is coupled into the first optical fiber and a fourth beam which is coupled into a first monitoring fiber;
a second beam splitter disposed between the second fiber port and the second condenser, wherein the second beam splitter is configured to split the second light beam into a fifth beam which is coupled into the second optical fiber and a sixth beam which is coupled into a second monitoring fiber;
a first optical sensor configured to detect an amount of a fourth beam output from the first monitoring fiber; and
a second optical sensor configured to detect an amount of a sixth beam output from the second monitoring fiber;
wherein the first monitoring fiber comprises a plurality of fibers, and
wherein the first optical sensor is configured to detect a position of the fourth beam among the plurality of fibers.

14. The ophthalmic endo-illumination system of claim 13 further comprising a processor configured to:
determine a coupling efficiency of the fifth beam at the second optical fiber based on the amount of the sixth beam output detected at the second monitoring fiber.

15. The ophthalmic endo-illumination system of claim 14 further comprising a power monitor configured to detect an amount of the light beam produced at the light source.

16. The ophthalmic endo-illumination system of claim 15, wherein the processor is further configured to determine whether a decrease in the amount of the fifth beam output detected at the second monitoring fiber is caused by a decrease in the coupling efficiency at the second condenser or caused by a decrease in the amount of the light beam produced at the light source based on detection signals received from the power monitor, the first optical sensor, and the second optical sensor.

17. A method comprising:
coupling a light beam by a condenser through a beam splitter to split the light beam into a first beam which is coupled to an optical fiber of an ophthalmic endo-illumination probe and a second beam which is coupled to a monitoring fiber, wherein the monitoring fiber comprises a plurality of fibers;
detecting, by an optical sensor, an amount of a second beam output from the monitoring fiber, wherein the optical sensor is configured to detect a position of the second beam among the plurality of fibers; and
determining a coupling efficiency of the first beam at the optical fiber based on the amount of the second beam output detected at the monitoring fiber.

18. The method of claim 17 further comprising generating a notification notifying a user when the coupling efficiency of the first beam at the optical fiber is below a predetermined value.

19. The method of claim 17 further comprising adjusting a position of the condenser to maintain the coupling efficiency of the first beam at a predetermined value.

* * * * *